(12) United States Patent
Venkatramana et al.

(10) Patent No.: US 8,759,513 B2
(45) Date of Patent: Jun. 24, 2014

(54) POLYMORPHIC FORM OF RIFAXIMIN AND PROCESS FOR ITS PREPARATION

(75) Inventors: Sumangala Venkatramana, Mangalore (IN); Vijesh Alanthatta Madathil, Mangalore (IN); Pejala Kakrannaya Vasudeva, Mangalore (IN); Thangavel Arulmoli, Mangalore (IN)

(73) Assignee: Sequent Scientific Limited, Bangalore (IN)

( * ) Notice: Subject to any disclaimer, the term of this patent is extended or adjusted under 35 U.S.C. 154(b) by 0 days.

(21) Appl. No.: 14/003,612

(22) PCT Filed: Aug. 24, 2011

(86) PCT No.: PCT/IN2011/000573
§ 371 (c)(1),
(2), (4) Date: Sep. 6, 2013

(87) PCT Pub. No.: WO2012/035544
PCT Pub. Date: Mar. 22, 2012

(65) Prior Publication Data
US 2014/0012001 A1    Jan. 9, 2014

(51) Int. Cl.
*C07D 498/22*    (2006.01)

(52) U.S. Cl.
USPC .......................................................... 540/455

(58) Field of Classification Search
USPC .................................... 540/455, 457
See application file for complete search history.

(56) References Cited

U.S. PATENT DOCUMENTS

| 4,341,785 | A  | 7/1982 | Marchi et al. |
|---|---|---|---|
| 7,045,620 | B2 | 5/2006 | Viscomi et al. |
| 7,709,634 | B2 | 5/2010 | Kothakonda et al. |
| 2008/0262220 | A1 | 10/2008 | Viscomi et al. |
| 2009/0082558 | A1 | 3/2009 | Kothakonda et al. |
| 2010/0137580 | A1 | 6/2010 | Vecchio et al. |

FOREIGN PATENT DOCUMENTS

| EP | 0161534 | 11/1985 |
|---|---|---|
| EP | 1698630 | 9/2006 |
| GB | 2079270 | 1/1982 |
| WO | 2009108730 | 9/2009 |

*Primary Examiner* — Charanjit Aulakh
(74) *Attorney, Agent, or Firm* — Kramer Amado, P.C.

(57) ABSTRACT

The present invention discloses a stable amorphous form of Rifaximin characterized by having X-ray powder diffraction pattern as given in FIG. 1, having a 2θ peaks at 7.2 and having moisture content in the range of 3% to 4% preferably, 3.4% to 3.7%. This invention also discloses a novel process for its preparation.

10 Claims, 2 Drawing Sheets

POLYMORPHIC FORM OF RIFAXIMIN AND PROCESS FOR ITS PREPARATION

FIELD OF INVENTION

Figure 1:
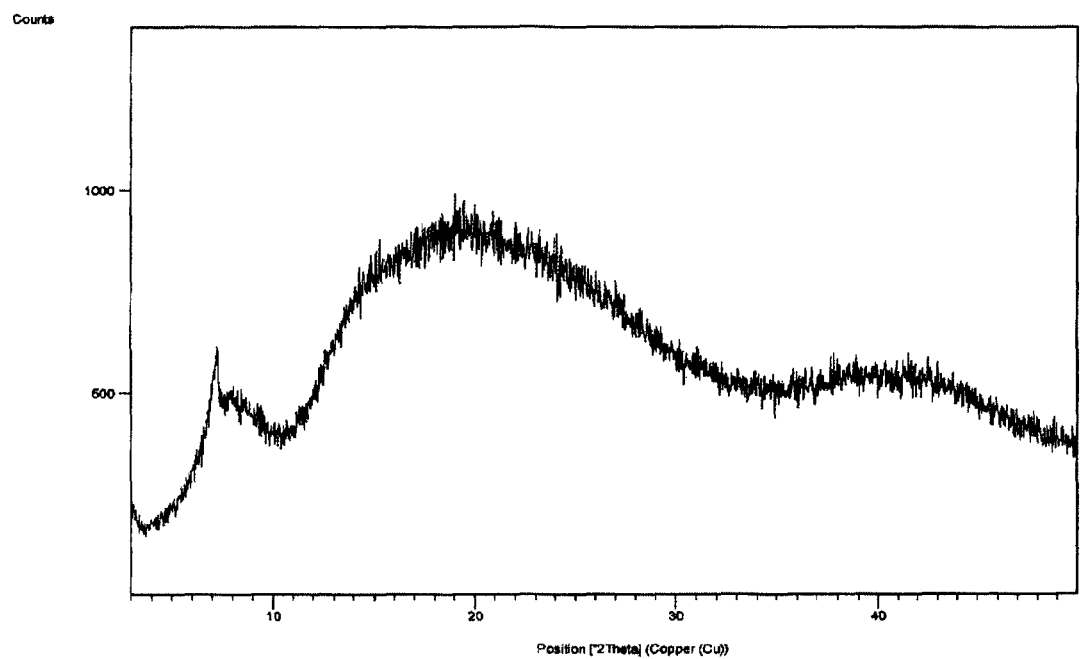

The present invention relates to a novel stable amorphous form of rifaximin and its process for preparation by dissolving in a solvent without using an antisolvent.

BACKGROUND OF THE INVENTION

Rifaximin, chemically known as {(2S,16Z,18E,20S,21S, 22R,23R,24R,25S,26S,27S,28E)-5,6,21,23,25-pentahydroxy-27-methoxy-2,4,11,16,20,22,24,26-octamethyl-2,7-(epoxypentadeca-[1,11,13]trienimino)benzofuro[4,5-e] pyrido[1,2-α]-benzimidazole-1,15(2H)-dione, 25-acetate} represented by formula I, is a semisynthetic rifamycin-based non-systemic antibiotic. It is marketed in the US as Xifaxan™ by Salix Pharmaceuticals.

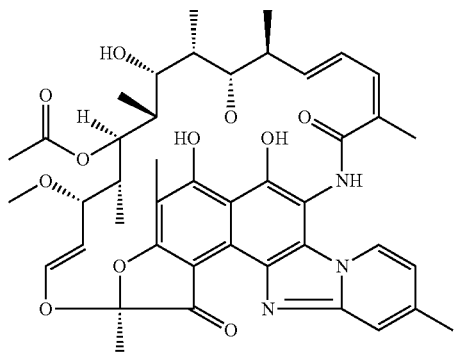

Formula I

It is useful for the treatment of travellers' diarrhoea in adults and in children 12-years or more of age caused by *E. coli* bacteria. Rifaximin has also been evaluated for the treatment of irritable bowel syndrome, diverticular disease, hepatic encephalopathy, pyogenic skin infections, and as an antibacterial prophylactic prior to colon surgery.

Structurally rifaximin is a pyrido-imidazo derivative of 4-deoxy-4'-methylpyrido[1',2':1,2]imidazo[5,4-c]rifamycin SV (Rifamycin SV). Unlike other Rifamycin SV derivatives, rifaximin exerts broad spectrum activity and has a specific mode of action which results in low gastrointestinal absorption.

GB 2079270 discloses imidazo-rifamycin derivatives having antibacterial activity, prepared from 3-halorifamycin S. U.S. Pat. No. 4,341,785 and EP 0161534 describe the processes for preparation of pyrido-imidazo rifamycin starting from rifamycin O. These patents describe a method for the purification of rifaximin using solvent systems comprising methylene chloride, chloroform, methanol, ethanol, isopropanol and water as an anti-solvent without disclosing the polymorphic form of the obtained Rifaximin.

U.S. Pat. No. 7,045,620 describes three polymorphic forms of rifaximin named as α-, β-, and γ-form. These forms are characterised by the different water contents and different 2θ values in powder X-ray diffractogram (PXRD) analysis. These forms are inter-convertible and, therefore, obtaining a specific polymorphic form is dependent on the drying conditions. The γ-form of U.S. Pat. No. 7,045,620 is described as poorly crystalline with a high content of amorphous component. It is characterized by water content between 1.0% and 2.0% and having a PXRD diffractogram containing three significant 2θ peaks at 5.0, 7.1 and 8.4. This form is prone to conversion to other polymorphic forms on exposure to atmosphere due to the change in its water content level. Thus this form is not preferred for formulation and it is highly desirable to have an active pharmaceutical ingredient which is polymorphically stable and suitable for pharmaceutical applications.

EP1698630 reported two new polymorphic forms δ- and ε-forms which are crystalline and there is a significant degree of overlap with the other reported forms.

U.S. Pat. No. 7,709,634 reported an amorphous form of rifaximin having two PXRD peaks at 2θ values 7.2° and 15.0°. This patent also discloses a process for its preparation by dissolving crude rifaximin in a solvent, precipitation by adding antisolvent, isolating and drying. This process uses preferably heptanes and methyl Tertiary butyl ether (MTBE) as an antisolvent.

U.S.2009/0312357 describes an amorphous rifaximin and its preparation. This amorphous rifaximin is prepared by stirring the crude rifaximin with a mixture of 20% dichloromethane and heptane at room temperature for 30-45 minutes and further washing with mixture of 20% dichloromethane and heptanes and drying under vacuum below 40° C. This process also uses multiple antisolvent.

Thus it is highly desirable to prepare a stable polymorphic form of rifaximin which is suitable for pharmaceutical formulation and prepared without using water or an antisolvent. The present inventors have developed a process which is robust and avoids water and antisolvent for preparing a novel amorphous rifaximin, which is stable chemically and polymorphically on storage and is unaffected by external parameters such as ambient humidity.

SUMMARY OF THE INVENTION

According to the principal aspect, this invention provides a novel stable amorphous form of rifaximin characterised by having X-ray powder diffraction pattern as given in FIG. 1 and having a 2θ peaks at 7.2.

According to another aspect of the invention the amorphous rifaximin is having moisture content in the range of 2.75% to 4% preferably, 3.4% to 3.7%.

Another aspect of the invention is to provide a process for preparation of the stable amorphous rifaximin comprising:
 a) dissolving crude rifaximin in a solvent selected from $C_1$ to $C_4$ alcohols;
 b) precipitating the rifaximin by cooling the solution without adding any antisolvent; and
 c) isolating the rifaximin, filtering and drying at ambient temperature

BRIEF DESCRIPTION OF THE DIAGRAM/FIGURE

FIG. 1: Illustrates X-Ray diffractogram of the amorphous form of rifaximin

Figure 2:
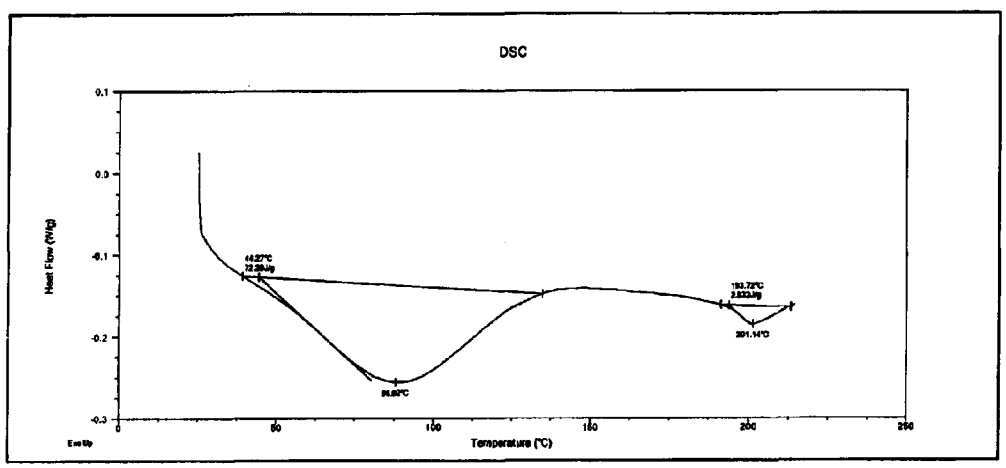

FIG. 2: Illustrates the differential scanning calorimetery thermogram of amorphous form of rifaximin

DETAIL DESCRIPTION OF THE INVENTION

Accordingly in an embodiment of the invention, the novel stable amorphous rifaximin of the invention is characterised by having X-ray powder diffraction pattern as given in FIG. 1 and having a 2θ peaks at 7.2 and having moisture content in the range of 2.75% to 4% preferably, 3.4% to 3.7%. The stable amorphous form of the invention is further characterised by the differential scanning calorimetery thermogram as given in FIG. 2.

In another embodiment of the invention, the amorphous rifaximin of this invention is very stable chemically and polymorphically on storage and is unaffected by external parameters such as ambient humidity as indicated by the PXRD spectroscopy.

In another embodiment of the invention rifaximin is dissolved in lower alcohols preferably $C_1$ to $C_4$ alcohols more preferably ethanol, isopropanol and 2-butanol, most preferably ethanol for the preparation of stable amorphous rifaximin. The crude rifaximin is dissolved in a solvent at a temperature between 0° C. to reflux, preferably at 40 to 60° C. The volumes used can be 1 to 25 volumes, preferably 1.5 to 12 volumes and most preferably 2 to 5 volumes. The dissolved reaction mass is cooled, preferably to 15-30° C. The product is precipitated without adding water or an antisolvent to the reaction mass. The precipitate is filtered and washed with ethanol and suck dried for 1 hour. The product is dried for 6 to 10 hours preferably for 8 hours at 45 to 80° C. most preferably at 70° C. under vacuum to have moisture content in the range of 2.75% to 4% preferably, 3.4% to 3.7%.

The following example serves to illustrate the present invention in more detail. They are, however, not intended to limit its scope in any manner.

EXAMPLES (a) Preparation of Rifaximin

Rifamycin O (50 g) and 76 ml of ethanol were stirred in a RBF at 20-30° C., for 15 minutes, DM water (100 ml) and 21.5 g of 2-Amino-4-picoline were added and stirred for 15 minutes at 25-30° C. The reaction mass was heated to 47° C. and stirred for 4-5 hours. Reaction mass was cooled to 20° C. and a solution of 1.32 g of ascorbic acid in 10 ml of concentrated HCl and 7.1 ml of DM water was added into it in 30 minutes. The reaction mixture was stirred for 30 minutes at 20° C.; ~8.75 ml of concentrated HCl was added into it to adjust the pH to 1.5-2.0 and further stirred. The crude was isolated by filtration, washed with 100 ml of 1:1 Ethanol and water mixture. The Crude was pulped with DM water until the pH of filtrate is neutral, dried for 10-12 hours at 70° C. until the moisture content was <5.0%.

(b) Purification of Rifaximin

Crude Rifaximin (50 g) was dissolved in 2.5 volume of ethanol at 57° C. and the clear solution was stirred for 15 minutes. The reaction mass was cooled to 25-30° C. in 5-6 hrs, stirred for 1 hour, filtered, washed with 0.5 volume of ethanol and suck dried for 1 hour. The product was dried for 8-10 hours at 70° C. under vacuum to get moisture content as 3.7%.

We claim:

1. Amorphous rifaximin characterised by having:
   substantially the same X-ray powder diffraction pattern as given in FIG. 1 and having a 2θ peak at 7.2; and
   a moisture content is in the range of 2.75% to 4%.

2. A process for preparation of amorphous rifaximin which comprises;
   a) dissolving crude Rifaximin in at least one solvent selected from the group consisting of $C_1$ to $C_4$ alcohols to produce a solution consisting of said Rifaximin and said at least one solvent;
   b) precipitating the rifaximin by cooling the solution without adding any antisolvent; and
   c) isolating the rifaximin by filtering and drying at ambient temperature.

3. A process according to claim 2, wherein the solvent is selected from the group consisting of methanol, ethanol, isopropanol, n-propanol, 2-butanol, and mixtures thereof.

4. A process according to claim 2, wherein the solvent is ethanol.

5. A process according to claim 2, wherein the precipitation is done by cooling to a temperature of between 15° C. and 30° C.

6. Amorphous rifaximin having a defined moisture content, said amorphous rifaximin having an X-ray powder diffraction pattern having a 2θ peak at 7.2; and
   said amorphous rifaximin being prepared by a process which comprises:
   a) dissolving crude Rifaxinain in at least one solvent selected from the group consisting of $C_1$ to $C_4$ alcohols to produce a solution consisting of said Rifaximin and said at least one solvent;
   b) precipitating the rifaximin by cooling the solution without adding any antisolvent; and
   c) isolating the rifaximin by filtering and drying at ambient temperature.

7. A process according to claim 2, wherein, the solvent is selected from the group consisting of methanol, isopropanol, n-propanol, 2-butanol, and mixtures thereof.

8. Amorphous rifaximin prepared by the process of claim 2, said amorphous rifaximin being characterised by having:
   differential scanning calorimetry peaks at about 92° C. and 201° C.; and
   a moisture content is in the range of 2.75% to 4%.

9. Amorphous rifaximin according to claim 6, wherein the moisture content is in the range of 2.75% to 4%.

10. Amorphous rifaximin according to claim 6, wherein the moisture content is in the range of 3.4% to 3.7%.

* * * * *